United States Patent [19]

Adams

[11] Patent Number: 4,582,065

[45] Date of Patent: Apr. 15, 1986

[54] ULTRASONIC STEP SCANNING UTILIZING UNEQUALLY SPACED CURVILINEAR TRANSDUCER ARRAY

[75] Inventor: Darwin P. Adams, Guilford, Conn.

[73] Assignee: Picker International, Inc., Cleveland, Ohio

[21] Appl. No.: 625,841

[22] Filed: Jun. 28, 1984

[51] Int. Cl.$^4$ ............................................. A61B 10/00
[52] U.S. Cl. ..................................... 128/660; 73/626; 358/112; 358/140; 310/335
[58] Field of Search ................ 73/620, 619, 625, 628, 73/641, 626; 128/660, 661, 662, 663; 358/112, 140; 343/5 SC; 310/335

[56] References Cited

U.S. PATENT DOCUMENTS

| | | | |
|---|---|---|---|
| 3,703,652 | 11/1972 | Noda | 310/335 |
| 3,765,018 | 10/1973 | Heard et al. | 343/5 SC |
| 3,881,164 | 4/1975 | Kossoff | 128/660 |
| 3,911,730 | 10/1975 | Niklas | 73/619 |
| 4,242,912 | 1/1981 | Burckhardt | 73/626 |
| 4,254,661 | 3/1981 | Kossoff et al. | 73/625 |
| 4,281,550 | 8/1981 | Erikson | 128/660 |
| 4,344,327 | 8/1982 | Yoshikawa et al. | 128/661 |
| 4,368,643 | 1/1983 | Tachita et al. | 73/626 |
| 4,399,702 | 8/1983 | Suzuki | 73/628 |
| 4,409,982 | 10/1983 | Plesset et al. | 128/660 |
| 4,434,437 | 2/1984 | Strolle et al. | 358/140 |
| 4,485,321 | 11/1984 | Klicker et al. | 310/332 |
| 4,516,583 | 5/1985 | Richard . | |

OTHER PUBLICATIONS

Metherell, A. F. et al., 1967 Proceedings of the International Symposium on Acoustical Holography, "Acoustical Imaging", vol. 8, pp. 97–117, Plenum Press 1976.
Thurstone, F. L., et al. "A New Ultrasound Imaging Technique Employing Two-Dimensional Electronic Beam Steering", Department of Biomedical Engineering, Duke University, pp. 249–259.
Havlice et al. "Medical Ultrasonic Imaging: An Overview of Principles and Instrumentation", Proceedings of the I.E.E.E., vol. 67, No. 4, Apr., 1979.
Lancee, et al. "Construction of a Circular Ultrasonic Array with Miniature Elements for Cardiac Application", Proceedings of the Second European Congress on Ultrasonics in Medicine, Munich, Germany (May 12–16, 1975) pp. 49–53.
Lancee et al. "An Ultrasonic Intracardiac Scanner", Ultrasonics, Mar., 1972, pp. 72–76.

Primary Examiner—Kyle L. Howell
Assistant Examiner—Ruth S. Smith
Attorney, Agent, or Firm—Watts, Hoffmann, Fisher & Heinke Co.

[57] ABSTRACT

An electronically step scanned real time ultrasonic imaging system and method is disclosed. The system includes a transducer assembly having an unequally spaced array of elements, each with an axis of transmission along which it transmits its main ultrasonic energy when electrically stimulated. The elements are disposed in a curvilinear array, wherein their axes of transmission are approximately co-planar, but divergent in the common plane. In the preferred embodiment, the axes of transmission diverge from one another by unequal angles, such that the tangent functions of each of the angles varies in equal increments along the array. Scan conversion techniques are used for displaying purposes, operating in the Y $\theta$ and Y tan $\theta$ formats.

15 Claims, 10 Drawing Figures

ULTRASONIC STEP SCANNING UTILIZING UNEQUALLY SPACED CURVILINEAR TRANSDUCER ARRAY

DESCRIPTION

1. Technical Field

This invention relates to the field of ultrasonic imaging equipment, and more particularly to an ultrasonic medical diagnostic system employing an improved transduc;er assembly and examination method.

2. Background Art

In recent years, the field of diagnostic ultrasound has seen the emergence of a so called "real time" ultrasonic B scanning examination system. The term "real time" means that the systems produce successive images at a rapid enough rate so that images are generated faster than the retention rate of the human eye so that moving objects appear in continuous motion. Thus, in real time operation, the course of the study can be influenced by the operator contemporaneously with the actual study, based on his observation of the rapidly produced image succession. This real time feature is considered an improvement over previous forms of ultrasonic examination, in which only a single image is developed slowly and gradually during the course of a study by moving a single transducer about the patient's skin. In addition to allowing the operator to influence the course of the study, real time systems allow for "stop action" images of moving body parts, and also for motion studies.

Real time ultrasonic examination systems have mainly fallen into two general types, i.e., linear scanning and sector scanning. Electronic linear scanning systems utilize a transducer assembly including a large linear array of individual piezoelectric ultrasonic transducer elements. Imaging circuitry fires a succession of different groups of elements in accordance with a predetermined repeated sequence. This produces a succession of resultant ultrasonic beams propagated along respective parallel paths extending outwardly from the transducer assembly. The assembly is held stationary against the patient's body during image generation.

This technique, in conjunction with known forms of imaging circuitry and display apparatus, produces from received ultrasonic echoes information defining a two dimensional rectangular image of the internal body structure of the patient taken in a common plane, or "slice" through part of the body near the transducer array. One coordinate of each point on the image plane is determined by the amount of time required for incident ultrasonic energy to be reflected back to the transducers from a tissue interface within the body. The other coordinate is determined by the location, along the transducer array, of the axis of the resultant ultrasonic beam which caused the reflected energy.

By operating this system to repeatedly step the incident beam origin along the linear transducer array at, for example, thirty repetitions per second, the rapid sequence of ultrasonically produced image frames which result can show motion of a moving body part. Alternately, a single frame of image data can be held for display, in order to stop rapid motion of such a body part.

The display area scanned by such linear step scanners is rectangular and suitable for presentation on a two dimensional display system, such as a CRT. The electronics required for such a system are relatively inexpensive and simple, since all the beams are parallel and stepped over uniform increments. Moreover, linear stepped scanning systems exhibit substantially uniform field of view throughout their display area.

Linear systems, however, do have some disadvantages. For example, the transducer assembly must of necessity be rather long, and therefore clumsy to use, since the length of one side of the rectangular display equals the length of the transducer array. Since all the ultrasonic beams produced by the linear scanner are propagated along parallel lines, the linear scanner is not generally capable of imaging portions of the patient's body which are hidden behind other nearer portions, such as an organ which may, be located behind a rib.

A known type of electrically stepped linear array ultrasonic system is described in the following publication, which is hereby expressly incorporated by reference: Havlice, J. F., et al, "Medical Ultrasonic Imaging: An Overview of Principles and Instrumentation", Proceedings of the IEEE, Vol. 67, No. Apr. 4, 1979, pp. 620–641.

Another type of known real time electronic ultrasonic scanner is the electronic sector scanner. In such devices, a linear array of transducer elements is employed as in the case of linear step scanning. The length of the array, however, is considerably shorter than in the case of the step scanned linear device described above.

In using the electronic sector scanner, the transducer assembly is held stationary near the portion of the patient's body to be examined. All elements are repeatedly fired in a single group. Phase delay circuitry is associated with imaging circuitry which is utilized to control ultrasonic beam emission and reception by the transducer elements. By proper phase delay of respective elements, the ultrasonic beam repeatedly produced by the transducer array is "steered" at different angles to the face of the transducer assembly. The angle of the ultrasonic beams produced by successive firings of all the elements of the transducer array is repeatedly scanned in increments from one side to another, such that the successive ultrasonic beams collectively sweep through the patient's body at different angles in a common plane.

Several advantages over the linear stepped scanner are achieved by use of the electronic sector scanner. First, the transducer assembly is significantly more compact than in the case of the stepped scanner, and can thus be used at almost any location on the patient's body. Since the ultrasonic beams are directed into the subject at different angles, the electronic sector scanner can image portions of the body which might be hidden from view of the linear stepped scanner because of their location behind other more opaque portions of the body, such as bone.

Electronic sector scanning, however, does have its own inherent disadvantages. One such disadvantage is that these scanners have a narrow field of view in regions of the body close to the transducer assembly. This is because the field of view of the sector scanner resembles a sector of a circle and, close to the transducer assembly, the excursion of the sweep of the ultrasonic beam is quite small.

Another disadvantage of the electronic sector scanner is the relatively high cost of such units, due in large measure to the complexity of the electronics necessary to achieve the delay scheme employed to effect beam steering. While a typical linear transducer step scanner costs in the neighborhood of $15,000 to $30,000, the corresponding range of cost for electronic sector scanners is about $65,000 to $100,000 each.

Mechanically steered real time linear and sector scanners, using oscillating or rotating single crystal transducers, have also been proposed. Such systems, however, suffer from relatively large physical size, and problems associated with reliability of the mechanical drive. They also usually require the transducer to be immersed in a fluid.

Known proposals for electronic and mechanical sector scanners are described in the above referenced Havlice, et al, publication.

Another system, a variant of ultrasonic step scanning, (Bushmann "New Equipment and Transducers for Ophthalmic Diagnosis", *Ultrasonics,* Vol. 3, pages 18 et seq, January-March, 1965,) has been proposed relating to ultrasonic examination of the eye. It is suggested to ultilize ten transducers arranged in an arc such that the ultrasonic beams emitted by each of the transducers mutually converge near the center of the eye ball. Pulsing circuitry is applied to separately fire each of the transducers in a sequence.

A disadvantage of this type of examination stems from the fact that tissue interface points within the patient's body which generate ultrasonic echoes may be struck by primary incident energy from more than one transducer. Each such point could thereby lack uniqueness of location on the image display, causing blurring.

This lack of unique location of multiply-struck interface points would be caused by inhomogeneity in the patient's body. Acoustic velocity differs among tissue types. If the time required for an ultrasonic echo from one transducer to return to that transducer from the subject point is different from the corresponding return time with respect to another transducer whose energy also strikes the point, the subject point will show up at slightly different spots on the display.

It is an object of this invention to provide an economical ultrasonic scanning system having the flexibility, compactness and swept beam characteristics of an electronic sector scanner without the sector scanner's limited close up field of view and high price and which is susceptible of use with scan converters having simplified Y $\theta$ and Y tan $\theta$ memory formats, preserving the uniqueness of display location each imaged point, all for the cost of a simple linear.

DISCLOSURE OF INVENTION

The ultrasonic scanning system of this invention overcomes or reduces the disadvantages of the stepped linear scanner as well as those of the electronic and mechanical sector scanners, while combining advantages of both.

A system embodying this invention includes an ultrasonic transducer element array, and imaging electronics coupled to actuate the transducer array for emitting incident ultrasonic energy and to convert received echoes to electrical signals. The system also includes appropriate display apparatus to convert the electrical signals to a visual image describing internal structure of the patient's body.

The transducer array has a curvilinear arrangement of its elements. The transducer elements are disposed with their axes of primary transmission being divergent within a common plane. This feature enables the system to direct ultrasonic energy beams into a patient's body at different angles depending on which elements are fired. This facilitates the obtaining of ultrasonic echoes from body tissue interfaces located behind body parts which would obscure such interfaces if the ultrasonic beams were parallel. The divergent beams also provide a larger imaged area than would exist with a linear scanner employing the same length array.

Another specific feature of this invention, involving the use of a curvilinear array of ultrasonic transducers, relates to the configuration of the array and to its particular adaptability to an especially efficient means of processing ultrasonically derived information into a visible image.

In accordance with this specific feature, the ultrasonic transducers are distributed at unequal intervals along the curvilinear path. More specifically, the transducers are distributed at such intervals that the respective tangent values of each angle of ultrasonic beam divergence relative to ultrasonic axis of the other transducer, differ from one another by equal increments. Thus, where the axes of ultrasonic propagation of a series of ultrasonic transducers diverges from that of the center transducer by angles $\theta_1, \theta_2 \ldots \theta_n$, the angles $\theta_1, \theta_2 \ldots \theta_n$ are chosen such that their respective tangents differ from one another by integral multiples of a constant.

Such an unequally spaced array of ultrasonic transducers facilitates processing of ultrasonically derived information into a visual image by means of particularly efficient scan conversion. In such an embodiment, the scan converter has a memory with each address being dedicated to a particular Y and tan $\theta$. In reproducing the image in a set of X,Y coordinates on a CRT monitor, the Y displacement of each event is read directly from the memory. The X displacement of the corresponding event is obtained by merely multiplying the Y displacement by the other value associated with the memory location from which the event data is sampled, namely Y-tan $\theta$.

These and other features of this invention will be understood in greater measure by reference to the following detailed description, and to the drawings, in which:

BEST MODE FOR CARRYING OUT THE INVENTION

Figure 1:
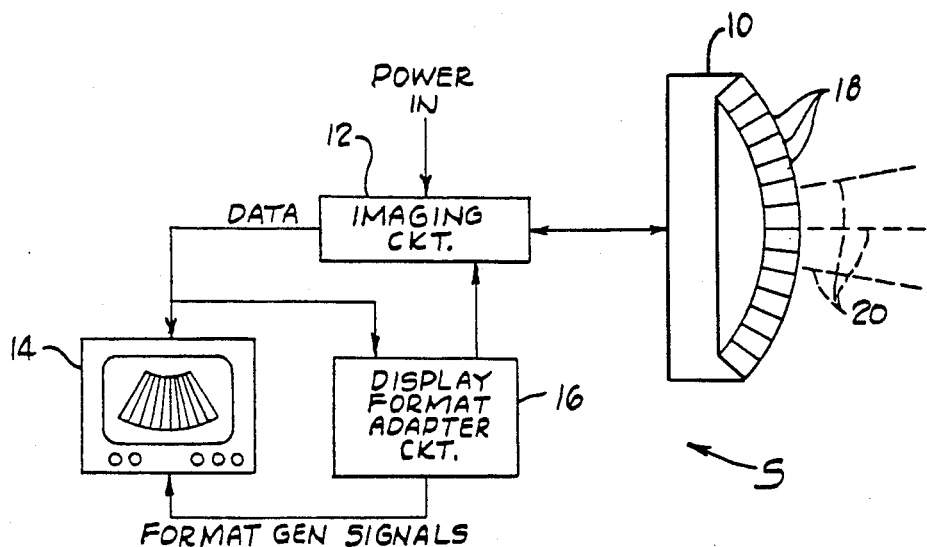
FIG. 1 is a generalized block diagram illustrating a prior art ultrasonic examination system incorporating the present invention.

FIG. 1 illustrates in general form a system S incorporating the present invention. The system S directs ultrasonic energy into a subject, such as a patient's body, and in response to echoes produced by the incident energy, produces an image representing internal structure or condition of the body.

The system S includes a curvilinear transducer assembly 10 for producing incident ultrasonic energy and for receiving echoes thereby caused. Imaging circuitry 12 actuates the transducer assembly to produce the incident energy, and receives electrical signals from the transducer produced in response to the echoes. Data from the imaging circuitry, in the form of these electrical signals, is directed to a display apparatus 14 which produces the image. Display format adaptor circuitry 16 provides format generating signals to the display apparatus 14, defining an array of image lines constituting the image, in response to data and timing control signals received from the imaging circuitry 12.

The transducer assembly 10 preferably includes 76 individual transducer elements, such as indicated by the reference character 18. Each transducer element comprises an individual piezoelectric ultrasonic transducer of known type, having a particular axis along which ultrasonic energy from the element is primarily directed. The ultrasonic transducer elements 18 are arranged in a curvilinear disposition along a circular arc. The axes of transmission of the elements, such as indicated by the dotted lines 20 in FIG. 1, diverge radially from the imaginary center of the circle defined by the arc along which the transducer elements are arranged.

In this preferred embodiment, the radius of curvature of the arc along which the transducer elements are disposed is approximately 10 centimeters (cm). The arcuate length of the transducer element array is approximately 5 centimeters.

The imaging circuitry actuates the transducer elements to produce short bursts of ultrasonic energy, each burst having a frequency of approximately 3.5 megahertz (MHz.). The imaging circuitry actuates a sequence of groups of transducer elements 18 such that resultant ultrasonic beams transmitted from the transducer assembly 10 scan the subject body in a sequence of different angles relative to the transducer assembly. This mode of scanning is of known type, and is sometimes referred to as "real time stepped ultrasonic scanning".

Echoes returning from tissue interfaces within the patient's body cause the transducer elements to produce electrical signals representing characteristics of those echoes. These electrical signals are received and processed by the imaging circuitry, which then directs them as data signals to the display apparatus 14, which may preferably comprise a cathode ray tube (CRT) display apparatus.

Preferably, the imaging circuitry 12 actuates or "fires" successive groups of 16 transducer elements each. The imaging circuitry 12 fires each group of transducers in a phased delay fashion, such that incident ultrasonic energy produced by the transducer assembly 10 is focused at a distance of approximately 4 centimeters from the transducer assembly. Additionally, the receiving periods of the members of each group of transducers are delayed in varying amounts in order to focus the zone from which echoes are received most readily at a distance of approximately 6 centimeters from the transducer assembly. These focusing delay characteristics are described in more detail below.

Display format adaptor circuitry 16 receives data and timing signals from the imaging circuitry 12, and produces format generating signals for causing the display apparatus 14 to produce a display comprising a number of divergent image lines collectively arranged in the form of radii of a truncated annulus. The arcuate length of the inner portion of the annulus display area (skin level) is approximately 5 centimeters, and the corresponding distance, or width, at the outer edge of the annulus (corresponding to the maximum range of about 20 cm.) is approximately 15 centimeters. Where the interior edge of the truncated annulus is located at the patient's skin line, the range of system operations is approximately 20 centimeters into the body. The included angle of the truncated annulus is approximately 30 degrees.

Figure 2:
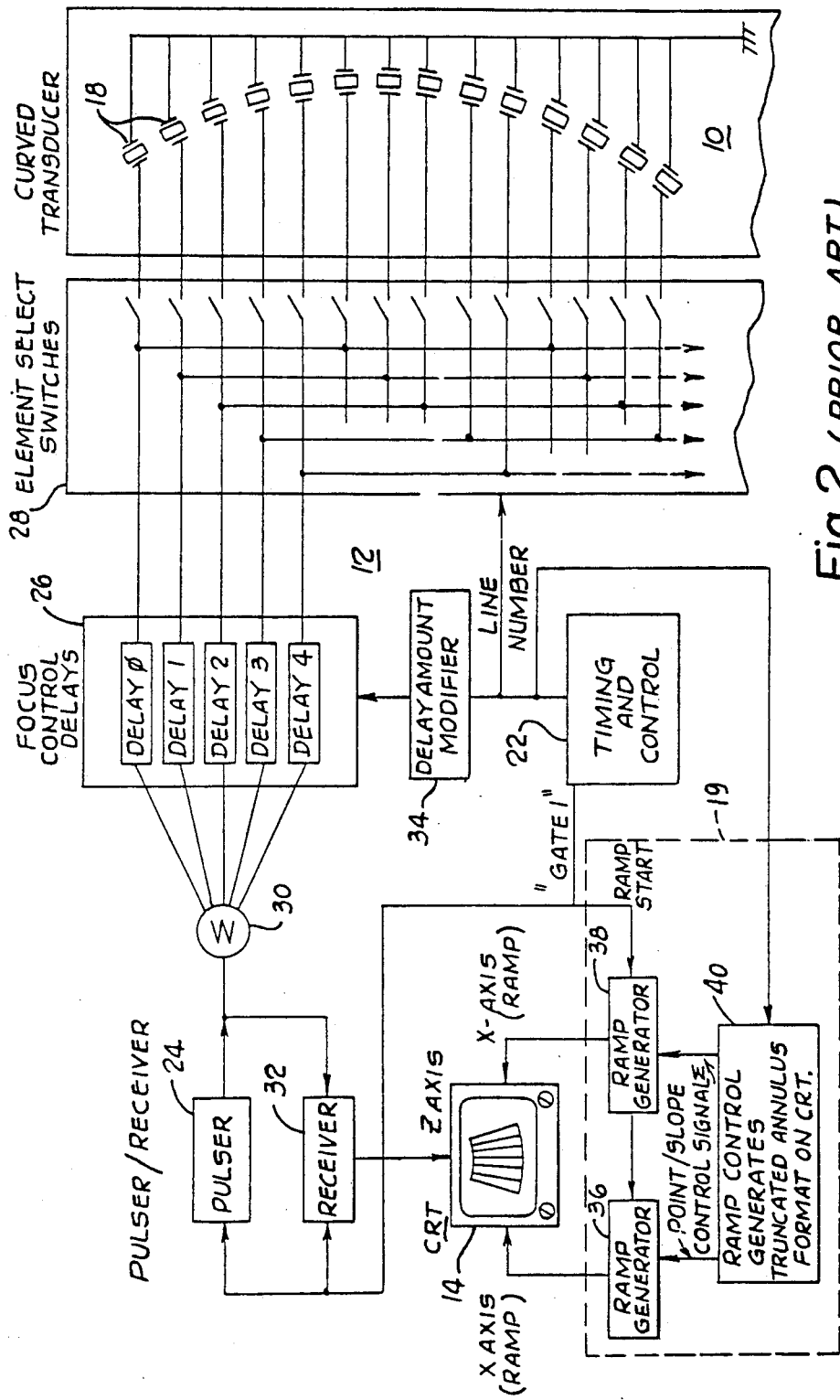
FIG. 2 is more detailed block diagram illustrating the system more generally exhibited in FIG. 1.

FIG. 2 illustrates in more detail an embodiment of an ultrasonic examination system incorporating the present invention. The imaging circuitry 12 includes timing and control circuitry 22 which sequences the operation of the remainder of the system S. The timing circuitry 22 actuates pulser circuitry 24 to fire the appropriate groups of transducer elements 18. Electrical signals from the pulsers 24 are transmitted along respective parallel signal channels to actuate the transducer elements 18 by way of delay control circuitry 26 and switching circuitry 28.

The switching circuitry 28 is controlled by the timing circuitry 22 to close appropriate members of the switching circuitry in order to govern the sequence of actuation of the transducer elements 18. Likewise, the focusing delay circuitry 26 is controlled by the timing and control circuitry 22 to impose delays on the various channels into which the pulser produces the actuation signals.

When echoes return to the respective transducer elements 18 which have been fired, the transducer elements convert the echoes to respective electrical signals. These received signals are transmitted back over each of the respective channels by way of the switching circuitry 28 and focus delay circuitry 26.

The focusing delay circuitry is controlled in the receive mode by the timing and control circuitry 22 to impose receiving delays upon the received signals. These receiving delays focus the receiving zone of the transducer elements 18 in phase delay fashion to enhance sensitivity of the system to echoes generated in a particular reception zone relative to the transducer position.

The received and delayed signals are passed through a summing circuit 30 and directed to receiver circuitry 32. The receiver circuitry 32 transmits the summed received signals to the "Z", or intensity control, input of the display apparatus 14, which preferably is embodied by a cathode ray tube device.

Delay modification circuitry 34, described in more detail below, is provided betwen the timing and control circuitry 22 and the delay focusing circuitry 26. The delay modification circuitry controls the delays interposed by the various delay elements in each channel, during both the transmit and receive modes, in order to impose the proper focusing delays on the various signals, taking into account the curvature of the transducer assembly 10.

The pulser, receiver, and summing circuitry, as well as the focusing delay circuitry, switching circuitry and timing and control circuitry are exemplified for example in the analogous circuitry of an ultrasonic examination system, Model LS1000, sold by Picker Corporation, Northford, Conn. U.S.A.

The display format adaptor circuitry 16 includes a pair of ramp generators 36, 38 and ramp control circuitry 40. The outputs of the ramp generators 36, 38 are coupled to the Y axis and X axis inputs, respectively, of the display apparatus 14. By proper adjustment by the ramp control circuit of the starting times, initial values, and slopes of the ramp signals produced by the ramp generators, an array of divergent radii having a common center can be generated on the screen of the display apparatus. As shown in FIG. 2, this array of lines provides a display in the format of a truncated annulus. Each of the divergent radii on the display corresponds in location to a respective one of the divergent ultrasonic beams generated in sequence by the transducer assembly 10.

Thus, the system produces a display in the form of a truncated annulus whose interior edge represents the patient's skin surface, at the face of the transducer assembly, and whose outer edge represents the maximum range of the system field of view. The use of the curvilinear transducer assembly, with its corresponding truncated annular display, provides a much larger field of view than was previously obtainable by the use of a linear transducer assembly having the same length of that of the novel curvilinear transducer assembly. This larger field of view is obtainable without the aid of electronic delay circuitry for changing the incident angle of the produced ultrasonic energy. The larger field is likewise obtainable without the use of mechanical sector scanning techniques which can be expensive and cumbersome.

In operation, the two ramp signals defining the slope of each line component of the display format are initiated in response to a signal appearing on the lead indicated "ramp start". The ramp start signal is produced by the timing and control circuitry 22, and is timed to be synchronized relative to the firing of the transducer elements by the pulser cirucitry 24. The ramp control circuitry 40 is controlled by a signal from the timing and control circuitry 22 appearing on the line "number" lead which identifies the particular radial line component of the image to be generated in response to information derived from the current firing of the pulser circuitry 24.

Preferably, the transducers are fired in groups of 16, and the pulser and delay circuitry correspondingly define 16 electrical channels. The system is operated to produce real time images at approximately 30 frames per second. Each image preferably comprises 120 lines. A 120 line image can be obtained, if desired, from a 76 element transducer assembly by the employment of known fractional stepping techniques, such as described in the following publication which is hereby expressly incorporated by reference: Yoshikawa, Y. et. al., "Scanning Methods in Electro-Scanning Ultrasonic Diagnostic Equipment".

As noted above, the incident ultrasonic energy produced in the transmit mode is focused by phase delay technique at 4 centimeters from the transducer array. The delay program for accomplishing this focusing, taking into account transducer array curvature, is defined in Table I:

| Transducer Group Elements | Delay (Nanoseconds) |
| --- | --- |
| 1 and 16 | 0 |
| 2 and 15 | 113 |

-continued

| Transducer Group Elements | Delay (Nanoseconds) |
| --- | --- |
| 3 and 14 | 210 |
| 4 and 13 | 290 |
| 5 and 12 | 355 |
| 6 and 11 | 403 |
| 7 and 10 | 437 |
| 8 and 9 | 453 |

Similarly, the reception focal zone is focused at approximately 6 centimeters from the transducer array. The delay program for accomplishing this delay in the receive mode is defined by the following Table II:

| Transducer Group Elements | Delay (Nanoseconds) |
| --- | --- |
| 1 and 16 | 347 |
| 2 and 15 | 261 |
| 3 and 14 | 187 |
| 4 and 13 | 125 |
| 5 and 12 | 75 |
| 6 and 11 | 38 |
| 7 and 10 | 13 |
| 8 and 9 | 0 |

Figure 3:
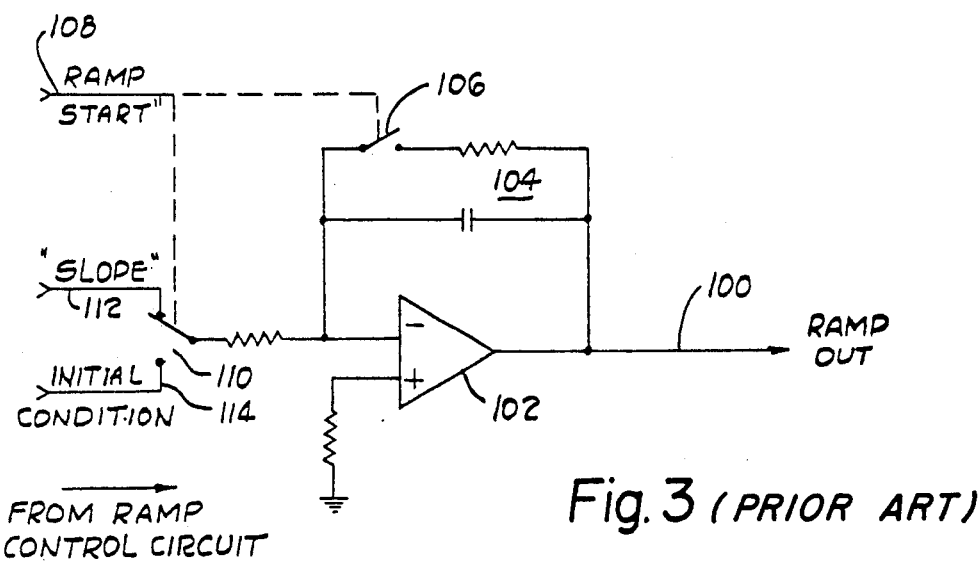
FIGS. 3-4 are schematic drawings illustrating portions of the system shown in block form in FIG. 2.
Figure 4:
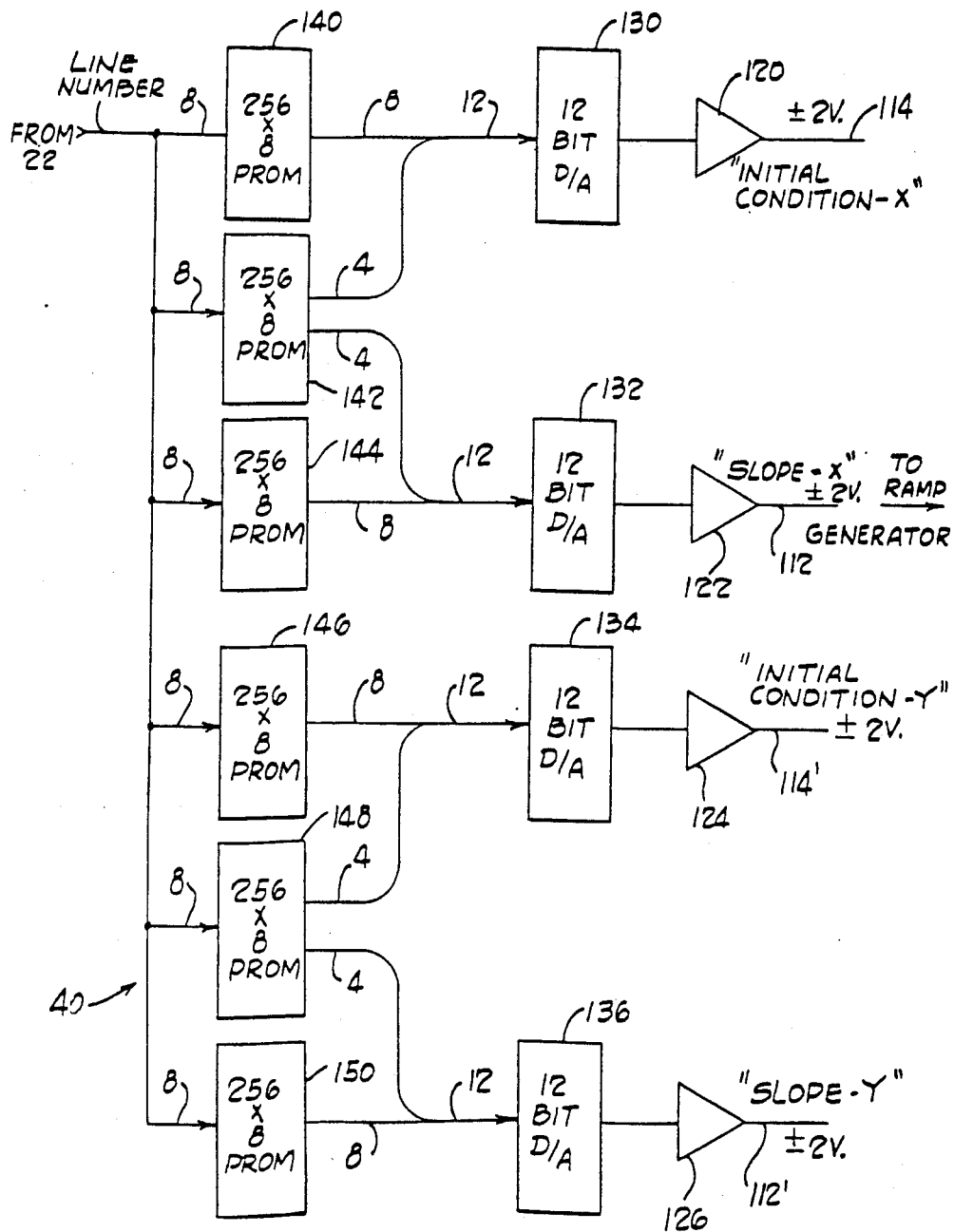

FIGS. 3 and 4 illustrate in schematic form the circuitry embodying the ramp generators 36, 38 and the ramp control circuitry 40.

FIG. 3 shows the schematic diagram of a ramp generator circuit. The ramp generator circuit of FIG. 3 corresponds to either of the ramp generator circuits 36, 38, their circuitry being identical. For purposes of simplicity, only one such ramp generator circuit is illustrated in detail.

The ramp generator circuit produces a ramp output voltage signal at a lead 100 which is the output of operational amplifier 102. Control over the ramp characteristics is influenced by the RC circuit 104 coupled between input and output of the amplifier 102. Closure of a switch 106 in the circuit 104 initiates production of the ramp signal. The switch 106 is closed by way of a signal appearing on "ramp start" input 108, generated by timing control circuitry 22.

Other signals, from the ramp control circuitry 40, govern aspects of the ramp signals generated at the lead 100. More specifically, a signal on a lead 112 defines the slope of the ramp signal generated. Another signal from the ramp control circuitry 40, appearing at a lead 114, governs the initial value of the ramp at its starting time.

Signals on the leads 112, 114 are input to the operational amplifier 102 by way of a two-position switch 110. The condition of the signal on the lead 108 controls the position of the switch 110. Prior to the initiation of the ramp signal output, the switch 110 is in its lower position, such that it defines the initial ramp signal value. Upon initiation of ramp signal production, the switch 110 is moved to its upper position, such that the ramp slope information input on the lead 112 is then applied to the operational amplifier 102, to control ramp slope.

The ramp generators 36, 38, conjunctively define the X,Y location of each radial image display line generated on the display screen. The ramp generators govern both the starting and ending position of each display image line, and its slope or path on the screen. The ramp generators perform this function by application of the ramp signals to the X and Y deflection plates, respectively, of the display CRT.

The slope of the actual display image line is a function of the ratio of the slopes of the respective ramp signals produced by the generators 36, 38. Thus, the slope of the image line displayed is distinct from, but a function of, the slopes of the individual ramp signals produced by the generators 36, 38.

The initial position of the trace of the image display line is determined by the initial values of the ramp signals produced by the two generators. Each initial position, in known fashion, provides the X,Y coordinate location of the beginning point of the corresponding image display line.

FIG. 4 illustrates in schematic form a preferable embodiment of the ramp control circuitry 40. The ramp control circuitry produces four outputs, two outputs directed to each of the ramp generator circuits 36, 38. The ramp control circuit outputs to each ramp generator an analog signal indicating the initial value of the ramp to be generated and the slope of that ramp. These signals are produced in response to a digital signal from the timing and control circuitry 22 indicating by number the particular image display line which is to be generated by the next ramp signals produced.

More specifically, signals appearing at the outputs 114, 112 indicate the initial value and slope, respectively, of the ramp signals to be produced by the ramp generator 38 for the image display line under consideration. Similarly, signals at the leads 114' and 112' define the analogous parameters for the Y axis ramp signal to be generated by the generator circuit 36.

The outputs on leads 114, 114' 112, 112' are produced by the operational amplifiers 120, 122, 124 and 126 as indicated in FIG. 4.

These operational amplifiers are fed input signals from the output of digital to analog converters, 130, 132, 134, 136, respectively. The inputs to the digital to analog converters are supplied as digital outputs from a series of six PROM (programmable read only memories) 140, 142, 144, 146, 148, 150. The function of the PROMS circuits is to receive a digital input identifying the line number of the individual display line to be produced in response to the immediately subsequent action of the ramp control circuitry 40. In response to each line number input to the PROMS, each PROM produces a preprogrammed unique digital signal.

The PROMS are programmed such that their digital signal outputs, as they are clocked by the "line number" digital signal, establish the proper initial conditions, ramp slopes and ramp timing to generate on the display the appropriate corresponding image line.

Figure 5:
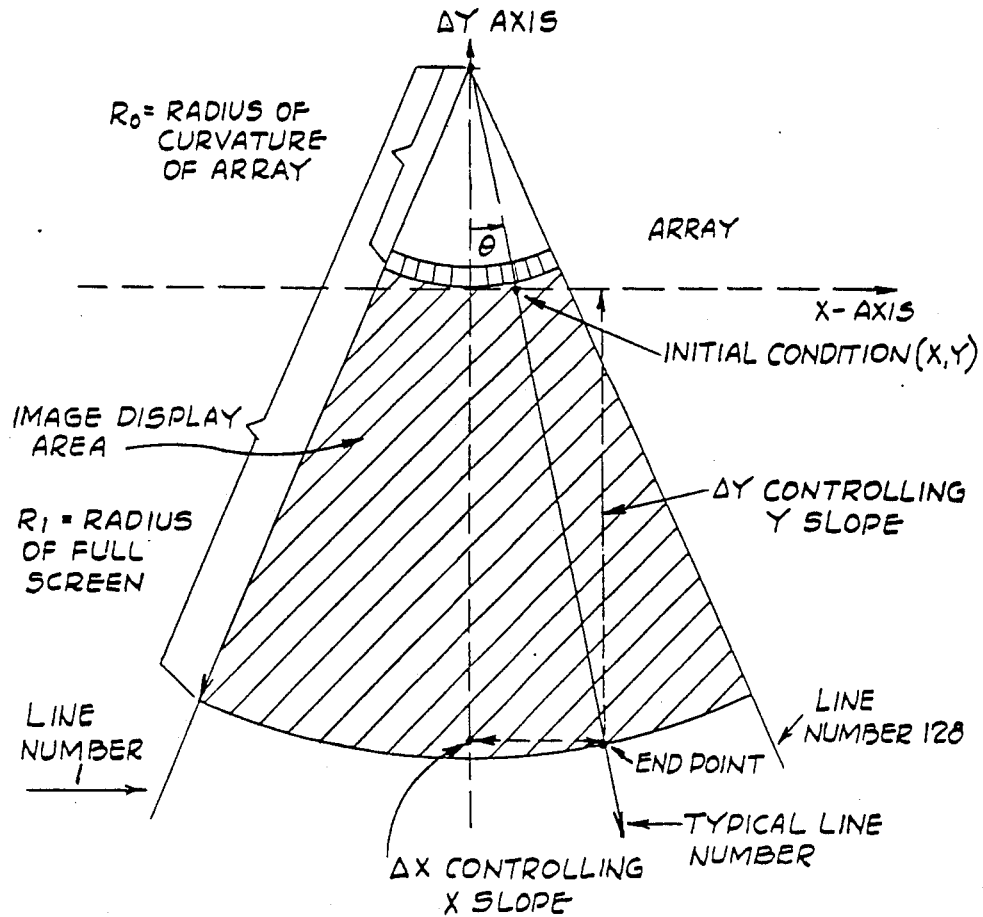
FIG. 5 is a graphical drawing illustrating mathematical parameters of components of the system shown in FIG. 2.

It is believed that those of ordinary skill in the art relevant to the subject matter discussed here would be able, by the use of ordinary trigonometry to provide appropriate programming for the PROMS by analyzing the geometry of each desired image display line individually. However, for those not intimately familiar with this art, FIG. 5 is provided, illustrating the mathematical consideration involved in programming the PROM to generate appropriate initial conditions and slopes for each respective display line. In the embodiment described in FIG. 5, the display is configured as a truncated annulus having several individual display lines. The angle $\theta$ varies in increments equal to the total angular excursion of the display area divided by the number of lines. The equations for programming each output for the PROMS corresponding to each individual display image line, are set forth near the bottom of FIG. 5. The initial conditions and slopes for both X and Y are determinable by substituting for $\theta$ each individual angle of each display image line which is desired to be produced. The embodiment of the display format adaptor circuitry 16 described above comprises analog circuitry. As a matter of choice, however, those of ordinary skill in the art may embody the display format adaptor circuitry 16 in a digital form.

Figure 6:
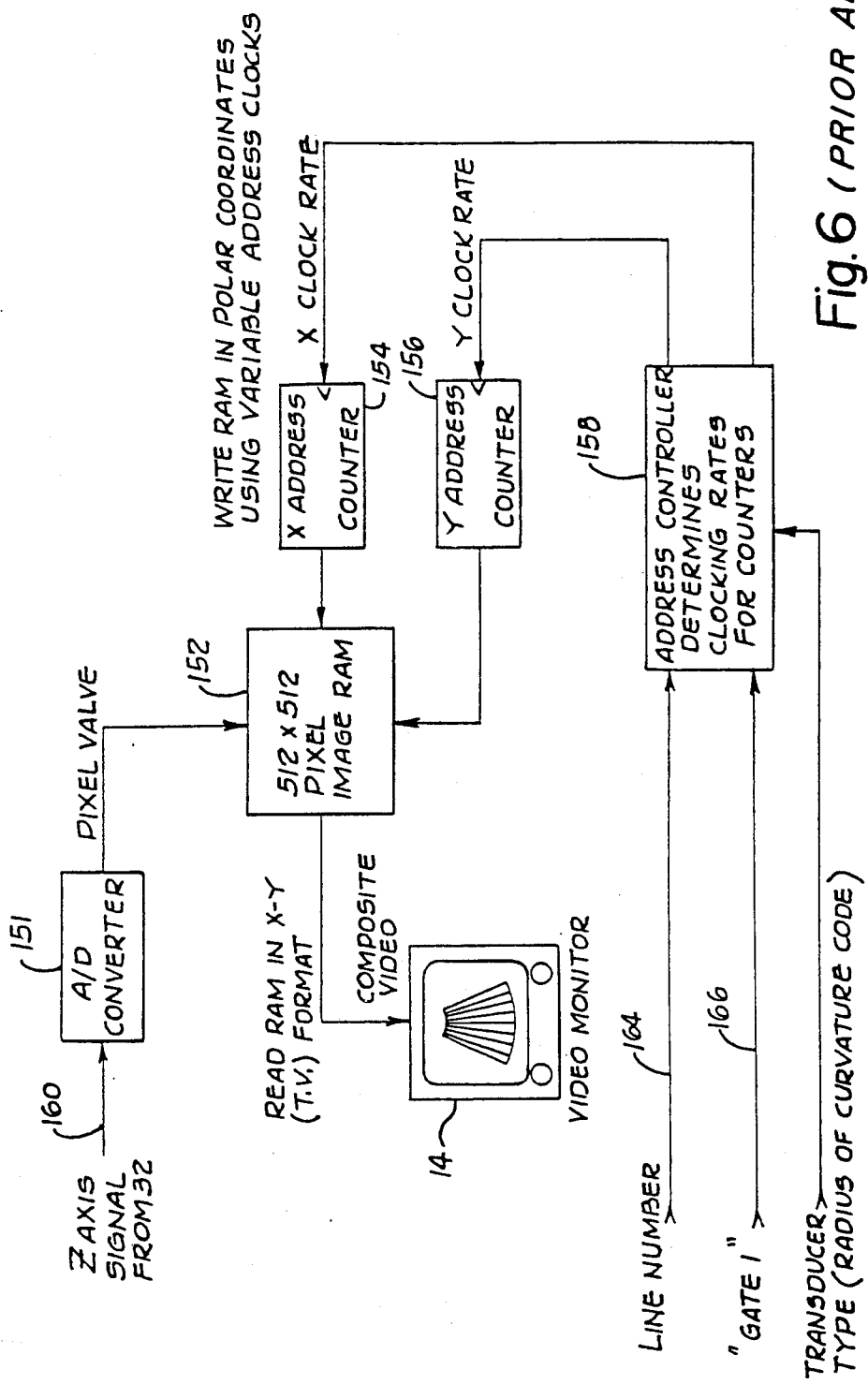
FIG. 6 is a block diagram illustrating an alternative embodiment portion of the system of FIG. 2.

More specifically, such an embodiment could suitably comprise a sector form digital scan coverter. A suggested embodiment for such a digital scan converter is illustrated in FIG. 6. The scan converter of FIG. 6 comprises an analog to digital converter 151, a random access memory 152, address counter circuitry 154, 156 and address counter control circuitry 158.

In operation, the "Z" signal from the receiver circuitry, appearing upon a lead 160, is converted to digital form by the converter 151 and presented to the random access memory (RAM). The address counters and counter control circuitry determine the address in the RAM at which the incoming digitized Z signal is to be placed. The address counters 154, 156 are used to write the RAM in polar coordinates. The counters are operated by variable address clock rate signals from the counter control circuitry 158. The counter control circuitry 158 operates in response to signals from the timing and control circuitry 22 appearing on the leads 164, 166. The signal on the lead 166 indicates the particular line of the composite image to, be currently displayed. The signal on the lead 166 is a synchronizing signal to synchronize the production of the displayed line relative to the firing of the transducers.

Conversion to polar coordinates R, $\theta$ from X, Y coordinates is in accordance with the relation $Y = R \cos \theta$. This conversion is achieved in known form by controlling clocking rates, in each of the embodiments that are described below.

When a digital representation of an image frame has been accumulated in the RAM by steering the incoming digitized Z axis signals among the appropriate RAM addresses, the RAM contents are read out in X,Y television format, and presented as inputs to a CRT video monitor display apparatus 14.

There are several ways in which ultrasonically derived data from the transducer array of this invention can be stored, processed and read out to form a visual display on a CRT monitor.

One system uses a so-called "X,Y" memory format, wherein each pixel, or image portion, on the display has a corresponding memory location, expressed in X and Y coordinates.

Figure 7:
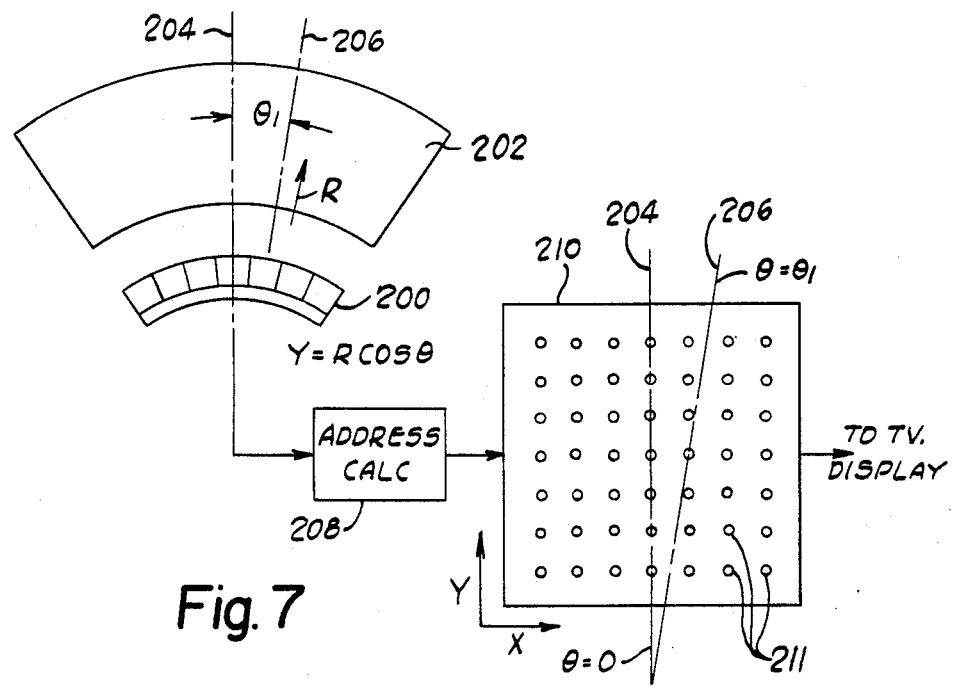
FIGS. 7-9 are partially graphical, partially block diagrams of ultrasonic systems incorporating specifi embodiments of the present invention.

FIG. 7 illustrates a curvilinear array 200 of ultrasonic transducers for directing ultrasonic energy upward, as shown in this Figure, into a field of view denoted as 202. FIG. 7 illustrates two lines 204, 206 of ultrasonic propagation, and illustrates the manner in which data from those two lines are written into the memory and subsequently processed to form an image in a CRT screen.

The line 204 emanates centered with the central one of the ultrasonic transducers of the array 200, and its angle of propagation is arbitrarily chosen as $\theta = 0$.

A memory 210 is provided having an array of memory address locations which can be characterized graphically as a two dimensional pattern of dots 211. In the memory 210, each column of dots, are shown in FIG. 7, is dedicated to a particular value of the X coordinate of the image pixel. Each row of elements is dedicated to a particular value for the Y coordinate of the pixel. Thus, each memory address stores an image amplitude value for an image region about a particular X,Y location.

Interposed between the curvilinear array 200 and the memory 210 is address calculator circuitry 208 whose function is described in more detail below.

Since the X coordinate of each point on line 204 = Y tan $\theta$, and $\theta = 0$ for line 204, the X coordinate of each point on line 204 = 0. It is thus quite simple to represent in the memory 210 each image pixel defined by the line 204, since X = 0 for each point on the line. The line 204 can be collectively represented by each of the memory addresses lying along the line 204 as defined in the portion of FIG. 7 describing the memory 210.

Line 206, however, diverges from line 204 by an angle $\theta_1$. Since not every point on the line 206 corresponds precisely to an address represented by one of the memory locations 211 of the memory 210, the scan converter hardware must choose which memory addresses are to be written into by information from the ultrasonic energy propagated along the line 206, and which are to be left unwritten. This necessitates the use of a fairly complicated hardware system comprising the address calculator circuitry 208 to make these decisions and to avoid generation of digital artifacts in the displayed image. The address calculator circuitry, in responding to data derived from ultrasonic energy propagated along the line 206, must often write each data point into the memory address most closely approximating the actual location of the structure which caused the generation of the data.

A description of this problem and its solution is provided by the publication Larsen, H., et al, "An Image Display Algorithm For Use In Real Time Sector Scanners With Digital Scan Converters", 1980 IEEE, Ultrasonics Symposium Proceedings, pp. 763-767, which publication is hereby expressly incorporated by reference.

In the system as illustrated in FIG. 7, data thus stored in the memory 210 can read out directly in X,Y format onto a CRT monitor to produce a visual display of an image corresponding to the information developed in response to ultrasonic energy emanating from the array 200.

Figure 8:
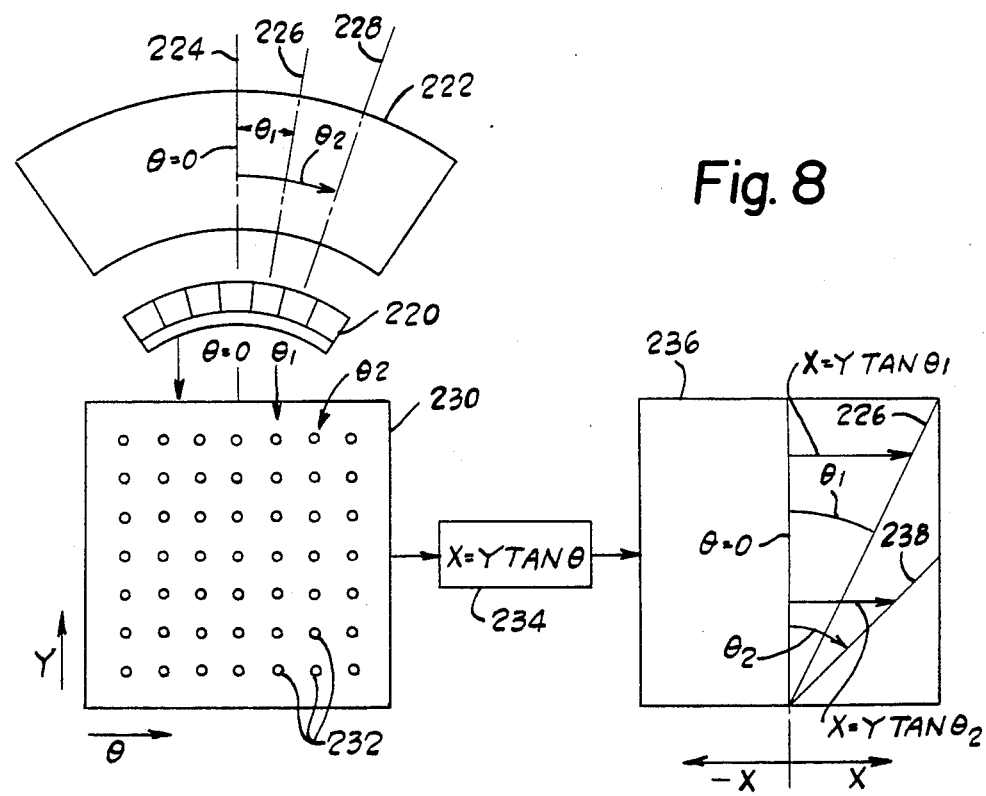

FIG. 8 illustrates another mode of scan conversion adaptable for use with the curvilinear array of this invention. FIG. 8 shows a curvilinear array 220 of ultrasonic tranducers, three of which, for example, propagate ultrasonic energy into a field of view along lines 224, 226, 228. As in the case of the FIG. 7 embodiment, energy propagated along the line 224 is arbitrarily assigned an angle $\theta = 0$. Energy propagated along the line 226 diverges from the energy of line 224 by an angle $\theta_1$, while energy propagated along the line 228 diverges from that of the line 224 by an angle $\theta_2$.

The embodiment of FIG. 8 employs a memory 230 having a structure similar to that of the memory 210 in FIG. 7, but with a different format of geometrical correspondence between the memory address locations 232 and the geometry of the field of view 222. Instead of being formatted in rectangular coordinates, the memory 230 is formatted in Y,$\theta$ coordinates. In memory 230, each column of address locations is dedicated to a particular angle $\theta$, while each row of address locations is dedicated to a particular value of the coordinate Y.

In FIG. 8, information from the memory 230 is read out through a calculation circuit 234 which subsequently transmits data to a CRT display 236, which produces a visual display corresponding to the information developed by propagation and reflection of the ultrasonic energy.

The system of FIG. 8 thus performs angle conversion between the memory and the display. This memory format is known as a "Y,$\theta$" format. In the Y,$\theta$ memory, there is a direct correspondence between the angle of divergence of the ultrasonic energy from each transducer element and memory location.

Each angle $\theta$ to which each column of memory address locations 232 is dedicated corresponds to one of the angles $\theta_1, \theta_2 \ldots \theta_n$ at which ultrasonic energy emanating from a particular ultrasonic element diverges from the angle $\theta = 0$.

In the embodiment of FIG. 8, the required conversion of data to the display is performed as the data is read from the memory.

In FIG. 8, each of the ultrasonic transducer elements is aimed at equally spaced angles $\theta_1, \theta_2 \ldots \theta_n$ with respect to $\theta = 0$, which is the orientation of the central element. When reading data from the memory into the display for producing the image, the address calculator distinguishes a particular Y and $\theta$ value for the data from each memory location. In order to generate the image on the display in a sector scanning format, each point in the memory is sampled and displayed on the CRT screen in a pattern described by the following relations: The Y coordinate on the display screen is simply the value for Y associated with the particular address location being sampled. The X coordinate is equal to the product Y x tan $\theta$.

This value, Y tan $\theta$, is provided by the address calculating circuitry 234. This circuitry is required to first calculate the tangent of the angle $\theta$ represented by the currently sampled memory location. The calculator circuitry then must produce a signal indicating the product of the tan $\theta$ times the Y value.

This information is then applied to the display 236 to produce an indication of the X and Y coordinates of the image point represented by the Y, $\theta$ value of the particular currently sampled memory address location 232 of the memory 230.

The coordinate conversion implemented by the embodiment illustrated in FIG. 8 can be computed to a high degree of accuracy by proper digital hardware design. As mentioned above, only two mathematical operations need be performed, i.e., a multiply function and a tangent function. This Y,$\theta$ technique reduces expensive memory costs and provides images which are essentially free of digital artifacts.

While the embodiments of FIGS. 6-9 are described in terms of only a single transducer element causing each ultrasonic energy line, this is done for simplicity and is not to be construed as limiting. Rather, each ultrasonic line can be a resultant line caused by phased or simultaneous firing of a different group of elements, as described above. Dynamic focusing can also be used.

Figure 9:
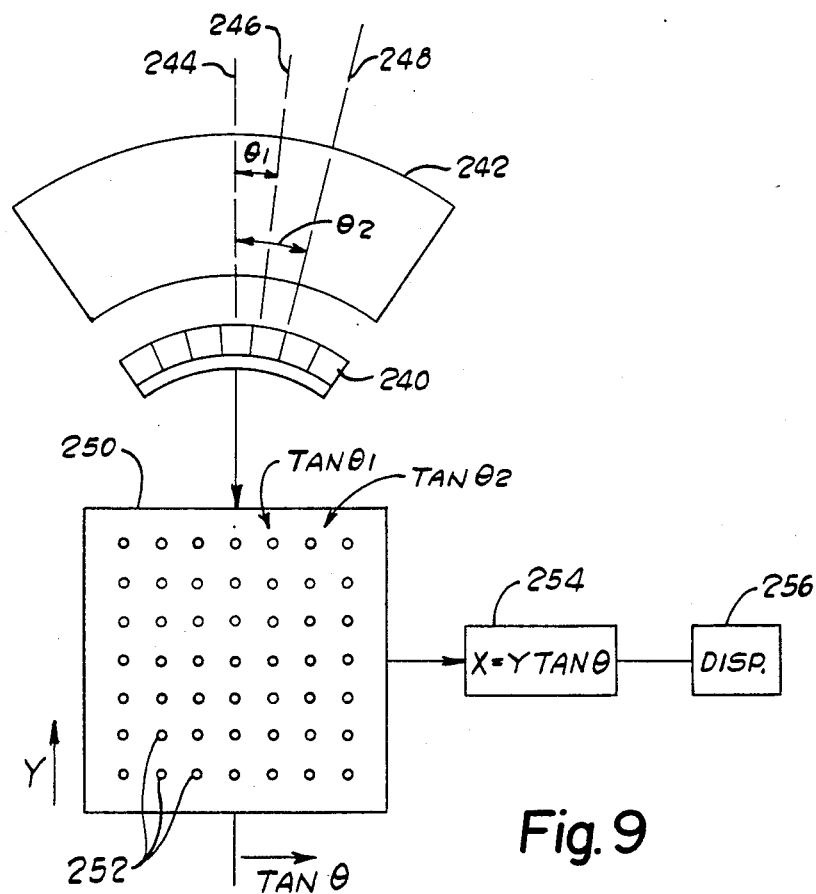

A third type of scan conversion technique is illustrated generally in FIG. 9. This technique even further simplifies the required hardware for producing the visual image, while providing high quality displays. This method uses a Y,tan $\theta$ memory format.

In the Y,$\theta$ memory system, as explained in connection with FIG. 8, data is acquired from the transducers at equal $\theta$ angle increments and stored in the memory under their correct $\theta$ coordinate. However, in the Y,tan $\theta$ system, data is acquired at unequal angles $\theta$, the angles $\theta$ having, however, equal tan $\theta$ increments.

FIG. 9 illustrates a system incorporating the Y,tan $\theta$ memory format. A curvilinear array 240 of ultrasonic transducers directs ultrasonic energy into a field of view 242, such as along lines 244, 246, 248. As in the instance of the system described in connection with FIG. 8, the line 244 of FIG. 9, being centrally located, is arbitrarily assigned an angle $\theta=0$. Lines 246, 248, diverge from line 244 by angles $\theta_1$ and $\theta_2$, respectively.

An important aspect of this format is that the angles of divergence between adjacent ultrasonic propagation axes, such as $\theta_1$, $\theta_2$, are not equal. Rather, the angles $\theta_1$, $\theta_2$ etc., are chosen such that the tangents of each of the respective adjacent angles $\theta$ differ by a constant increment across the field of view 242.

Data from the transducer array 240 is directed to a memory 250 having a plurality of memory locations graphically indicated by dots 252. Each of the columns of address locations in the memory 250 is dedicated to a particular value of tan $\theta$ corresponding to that tan $\theta$ value of one of the lines of ultrasonic propagation from the curvilinear array 240. Each of the rows of memory address locations is dedicated to a particular value of Y.

A calculator 254 samples data from each of the memory locations and develops X,Y coordinates for input to the CRT display 256. It can be seen from the foregoing that the only function the calculation circuitry must perform is the multiplication of the Y value times the tan $\theta$ value associated with each sampled memory address.

The Y coordinate of each displayed pixel is directly derived from the Y value to which the sampled address location is dedicated. To obtain the X value corresponding to that same location, the calculation circuitry need only multiply the Y value, already present in the memory, with the tan $\theta$ value, which is likewise already present. Thus, only a multiplication calculation must be made.

A scan converter employing the Y,tan $\theta$ memory format is identified as a model 672, manufactured by Hughes Aircraft of Carlsbad, Calif. U.S.A.

In the case of a sector format probe such as a mechanical sector scanner, having capability for propagating ultrasonic energy along only one axis at a time, the probe is directed, not to equal increments of angle $\theta$, but to increments of angle $\theta$ such that each function tan $\theta$ differs by equal increments from the tan $\theta$ of each of its adjacent angular positions. Under this format, the axes of ultrasonic transmission near the edges of the scan are spaced more closely in angle $\theta$ increments than they are near the center of the scan, i.e., where $\theta=0$.

Thus, the Y,tan $\theta$ memory format can minimize hardware costs, while at the same time providing high quality image displays.

Figure 10:
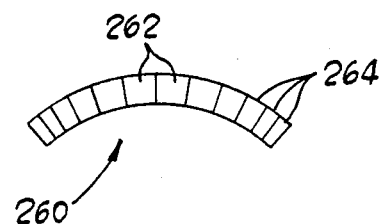
FIG. 10 is a plan view of a portion of an ultrasonic system which can be used in connection with the system illustrated in FIG. 9.

When using a Y,tan $\theta$ memory format with a convex curvilinear array such as described above, one must design that array to scan the ultrasonic energy at unequal $\theta$ intervals. A way to do this is to space the array elements unequally across the face of the transducer array. See FIG. 10, reference character 260. The amount of such spacing varies across the array, depending upon the angle $\theta$. The element spacing is designed such that the resultant ultrasonic axes correspond to the following mathematical relationships:

$$x = y \tan \theta \quad \theta = \tan^{-1} \frac{x}{y}$$

$$\frac{d\theta}{dx} = \frac{1/y}{1 + \left(\frac{x}{y}\right)^2} \quad \frac{d\theta}{d(x/y)} = \frac{1}{1 + (x/y)^2}$$

Or, expressing in $\theta$, since $\frac{x}{y} = \tan \theta$ $$\frac{d\theta}{d(x/y)} = \frac{1}{1 + \tan\theta^2}$$

Some examples of the ratio of spacing are as follows:

| $\theta$ | Spacing |
|---|---|
| 0° | 1.0 |
| ±7.5° | 0.983 |
| ±15° | 0.933 |
| ±30° | 0.750 |

For small angles $\theta$, the spacing changes very little across the array, as at 262. For larger angles, such as a 60° total scan angle (+or−30°) such as at the elements referred to at 264 a more significant change occurs with elements closely spaced at the ends of the array. If the spacing changes significantly with one selected group of elements used to generate one ultrasonic resultant line, compensation may be required in the electronic focusing circuitry to provide a well focused beam. A typical array might comprise a 5 centimeter (cm) array line with 15° curvature and 80 elements, using 15 elements at a time to generate each resultant line. This provides an effective aperture of 0.94 cm. When the scan is at the end of the array (7.5°) the spacing at this end will be 0.983, while at 15 elements inside of this point the spacing would be 0.993. Since each element is spaced from its neighbor by approximately one wavelength, the spacing error will be only in the order of one-tenth of a wavelength. This error can be easily accommodated.

It should be kept in mind that the foregoing disclosure is intended to be illustrative, rather than exhaustive, of the invention. Those of ordinary skill in the pertinent art may be able to make additions, deletions, or modifications to the preferred embodiment described above without departing from the spirit or scope of the invention, as defined in the appended claims.

I claim:

1. A medical diagnostic system for producing an image of a patient's internal body structure by the use of ultrasound, said system comprising:
   (a) a transducer assembly defining a curved array face and comprising a curvilinear array of ultrasonic transducer elements, said elements drawing unequally spaced respective transmission axes the face of said array;
   (b) imaging electronics means coupled to the elements in respective individual channels for causing the transducer elements to scan incident ultrasonic energy into the patient and to convert received echoes caused by the incident energy to electrical signals representing internal body structure of the patient, and
   (c) a display means coupled to the imaging electronics means and being responsive to the electrical signals for producing an image of the patient's internal body structure.

2. The system of claim 1, further comprising:
said ultrasonic transducer elements having respective mutually divergent principal axes of ultrasonic emission, said axes lying substantially in a single plane.

3. The system of claim 1, wherein:
said curvilinear transducer assembly configuration describes substantially an arc of a circle approximately 5 centimeters in length.

4. The system of claim 3, wherein:
said circle corresponding to said arc has a radius of about 10 centimeters.

5. The system of claim 1, wherein:
said transducer array comprises about 80 separate transducer elements.

6. The system of claim 1, wherein said imaging electronics comprises:
circuitry for focusing the reception characteristics of a set of said transducer elements to relatively enhance reception of echoes from a particular reception focal zone within the subject.

7. The system of claim 6, further comprising:
circuitry means for dynamically focusing groups of said transducer elements.

8. The system of claim 1, wherein:
(a) said transducer elements are arranged for defining axes of primary ultrasonic transmission, and
(b) adjacent ones of said axes of ultrasonic transmission are arranged to diverge from one another at angles whose tangent functions differ by equal increments.

9. The system of claim 1, wherein said imaging electronics comprises:
a scan converter having a Y,tan $\theta$ memory format.

10. An ultrasonic transducer assembly for use in a medical diagnostic system, said assembly comprising:
ultrasonic transducer means adapted to provide an image of a patient's internal body structure, said means comprising:
(a) a plurality of individual ultrasonic transducer elements; and
(b) mounting structure defining a curved array face for disposing said ultrasonic transducer elements in a convex curvilinear array with mutually divergent primary axes of ultrasonic transmission, said ultrasonic transducer elements having unequally spaced respective transmission axes along the transducer array face.

11. In an electrically scanning real time ultrasonic diagnostic system comprising:
(a) a probe defining a curved array face and having ultrasonic beam emitting surface, in which plural ultrasonic wave transducers are convexly arranged having unequally spaced respective transmission axes along said array face, and
(b) means coupled to said probe for energizing selected ones of the ultrasonic transducers according to a predetermined program.

12. The system of claim 11, wherein
(a) said transducers are arranged in an acruate shape at unequal distances along the arc, and
(b) said energizing means comprises a transmitting and receiving wave control circuit actuating said ultrasonic transducers as plural groups and repeatedly performing ultrasonic beam transmitting and receiving action with a program of ultrasonic directivities respectfully associated with each group.

13. An electronically scanned ultrasonic imaging system comprising:
(a) a transducer assembly comprising a curvilinear array of ultrasonic transducer elements arranged to define respective divergent unequally spaced axes of ultrasonic emission defining a plane, said adjacent ones of said axes diverging from one another by angles whose tangents differ by an equal amount;
(b) imaging electronics means coupled to the transducer assembly for causing selected transducer elements to emit ultrasonic energy into a subject and for converting received echoes caused by the incident energy to electrical signals representing an image of internal structure of the subject, said imaging electronics including a scan converter means having a Y, tan $\theta$ memory address format, circuitry means for sampling Y, tan $\theta$ values stored at each memory address, and calculator circuitry means for producing an X-coordinate signal corresponding to information at the sampled location by calculating the product of the Y and tan $\theta$ values stored at the memory address, and
(c) display hardware means coupled to the imaging electronics and responsive to said sampled Y values and to the calculated product of Y and tan $\theta$ to produce an image of internal subject structure whose point comprise the respectively developed X and Y coordinates corresponding to information from each sampled memory address.

14. A method for examining a subject by the use of ultrasound, said method comprising the steps of:
(a) transmitting scanned ultrasonic energy into a subject along paths which define substantially a single plane and diverge from one another at unequal angles, the angles of divergence of each path from its adjacent paths having tangents which differ by equal amounts from the tangent of the angle of said each path;
(b) converting echoes caused by the incident ultrasonic energy into electrical signals;
(c) storing said electrical signals in the memory of a scan converter having a Y,tan $\theta$ memory address format such that information stored at each memory address comprises an indication of the Y and tan $\theta$ values corresponding to polar coordinates of the location of the echo which caused generation of the information;
(d) sampling the contents of each memory address;
(e) calculating an indication of the Y and Y-tan $\theta$ values corresponding to the information at the sampled memory address;
(f) transmitting the Y and Y-tan $\theta$ indications to a display apparatus, and
(g) causing the display apparatus to display the sampled information in X,Y coordinates, the Y coordinate of each image point corresponding to the Y indication, and the X coordinate of each image point corresponding to the Y, tan $\theta$ value, of the sampled memory address.

15. A medical diagnostic system for producing an image of a patient's internal body structure by the use of ultrasound, said system comprising:
(a) a transducer assembly comprising an array of ultrasonic transducer elements, said elements mounted fixedly with respect to one another and being positioned such that the ultrasonic transmission axes of the respective elements diverge with unequal spacings (b) imaging electronics means coupled to the elements in respective individual channels for causing the transducer elements to scan incident ultrasonic energy into the patient and to convert received echoes caused by the incident energy to electrical signals representing internal body structure of the patient, and (c) a display means coupled to the imaging electronic means and being responsive to the electrical signals for producing an image of the patient's internal body structure.

* * * * *

UNITED STATES PATENT AND TRADEMARK OFFICE
CERTIFICATE OF CORRECTION

PATENT NO. : 4,582,065
DATED : April 15, 1986
INVENTOR(S) : Darwin P. Adams

It is certified that error appears in the above-identified patent and that said Letters Patent is hereby corrected as shown below:

Column 14, line 57, "drawing" should be --having--;
Column 14, line 58, after "axes" insert --along--;
Column 15, line 55, "surface" should be --surfaces--;
Column 15, line 63, "acruate" should be --arcuate--;
Column 16, line 30, "point" should be --points--;
Column 17, line 3, "spacings" should be spacing;--.

Signed and Sealed this

Twelfth Day of August 1986

[SEAL]

Attest:

DONALD J. QUIGG

Attesting Officer

Commissioner of Patents and Trademarks